United States Patent [19]

Friends et al.

[11] Patent Number: 4,652,622
[45] Date of Patent: Mar. 24, 1987

[54] POLYSILOXANE COMPOSITION WITH IMPROVED SURFACE WETTING CHARACTERISTICS AND BIOMEDICAL DEVICES MADE THEREOF

[75] Inventors: Gary D. Friends, Ontario; John B. Melpolder, Hilton; Jay F. Kunzler, Canandaigua; Joon S. Park, Pittsford, all of N.Y.

[73] Assignee: Bausch & Lomb Incorporated, Rochester, N.Y.

[21] Appl. No.: 633,309

[22] Filed: Jul. 23, 1984

Related U.S. Application Data

[62] Division of Ser. No. 489,921, Apr. 29, 1983, Pat. No. 4,495,361.

[51] Int. Cl.$^4$ ............................................. C08F 230/08
[52] U.S. Cl. .............................. 526/279; 526/303.1; 526/304; 351/160 R
[58] Field of Search ..................... 526/279, 303.1, 304; 351/160 R

[56] References Cited

U.S. PATENT DOCUMENTS

| 4,153,641 | 5/1979 | Deichert | 526/279 |
| 4,157,418 | 6/1979 | Heilmann | 526/304 |
| 4,172,934 | 10/1979 | Heilmann | 526/304 |
| 4,254,248 | 3/1981 | Friends | 526/279 |
| 4,327,203 | 4/1982 | Deichert | 526/279 |
| 4,341,889 | 7/1982 | Deichert | 351/160 R |

Primary Examiner—Paul R. Michl
Assistant Examiner—A. H. Walker
Attorney, Agent, or Firm—Bernard D. Bogdon; DeWitt M. Morgan

[57] ABSTRACT

The surface wetting characteristics of polysiloxanes prepared from monomeric polysiloxanes endcapped with activated unsaturated groups and modulus modifiers are improved by the inclusion of small amounts of an N-alkenoyl trialkylsilyl aminate. The improved polymeric compositions can be used to form hard, gas permeable contact lenses and other biomedical devices.

18 Claims, No Drawings

POLYSILOXANE COMPOSITION WITH IMPROVED SURFACE WETTING CHARACTERISTICS AND BIOMEDICAL DEVICES MADE THEREOF

This application is a division of application Ser. No. 489,921, filed Apr. 29, 1983, now U.S. Pat. No. 4,495,361.

BACKGROUND OF THE INVENTION

1. Field of the Invention

This invention relates to hard, gas permeable, biomedical devices including contact lenses prepared from polysiloxanes polymerized with a modulus modifier and an N-alkenoyl trialkylsilyl aminate wetting agent.

2. Prior Art Statement

U.S. Pat. No. 4,153,641 discloses contact lenses made from polymers and copolymers comprising poly(organo-siloxane) polymers and copolymers formed by polymerizing a poly(organosiloxane)monomer alpha, omega terminally bonded through divalent hydrocarbon groups to polymerized, free radical polymerizably activated, unsaturated groups forming a polymer in a crosslinked network. Additionally, specific comonomers are disclosed which include lower esters of acrylic and methacrylic acid, styryls and N-vinyl pyrrolidinone which may be copolymerized with the above described poly(organosiloxane) to form a copolymer. The instant invention preferred polysiloxane monomers include the same poly(organosiloxane)monomers described above.

U.S. Pat. No. 4,208,506 discloses soft contact lenses made from polymers and copolymers comprising polyparaffinsiloxane polymers and copolymers formed by polymerizing a polyparaffinsiloxane monomer alpha, omega terminally bonded through divalent hydrocarbon groups to polymerized, free radical polymerizably activated, unsaturated groups forming a polymer in a crosslinked network. Additionally, specific comonomers are disclosed which include lower esters of acrylic and methacrylic acid, styryls and N-vinyl pyrrolidinone which may be copolymerized with the above described polyparaffinsiloxane monomer to form a copolymer. The instant invention preferred polysiloxane monomers include the same polyparaffinsiloxane monomers described above.

U.S. Pat. No. 4,303,772 discloses polysiloxanyl alkyl esters of acrylic and methacrylic acids and its copolymerization with alkyl esters of acrylic, methacrylic acids and/or itaconate esters to produce highly permeable contact lens material. The copolymer preferably includes a crosslinking agent and hydrophilic monomer. Contact lenses manufactured from the material are easily machined and polished into hard or semi-hard contact lenses having excellent dimensional stability.

U.S. Pat. No. 4,330,383 discloses improved contact lens materials are obtained from copolymers containing a siloxanyl alkyl ester vinyl monomer by exposing the materials to high energy radiation thereby reducing the amount of unreacted monomer and residual contaminants.

U.S. Pat. No. 4,327,203 discloses articles for biomedical applications made from a polymer formed by polymerizing (a) one or more polysiloxane monomers alpha, omega terminally bonded through divalent hydrocarbon groups to an activated, unsaturated group with (b) a cycloalkyl modulus modifier, e.g. tertiary butylcyclohexyl methacrylate, menthyl acrylate or methylisopentyl cyclooctyl acrylate, and (c) a tear film stabilizer. The products are useful as hard contact lenses. U.S. Pat. No. 4,341,889 discloses the modulus modifier above can be tertiarybutyl styrene. U.S. Pat. No. 4,355,147 discloses the modulus modifier above can be a polycyclic acrylate or methacrylate such as isobornyl methacrylate, adamantyl acrylate or isopinocamphyl methacrylate.

SUMMARY OF THE INVENTION

In accordance with this invention, there is provided a class of new and novel N-alkenoyl trialkylsilyl aminates of the formula $$CH_2=C(E)C(O)N(H)CH(G)(CH_2)_mC(O)OSi(R)_3 \qquad (I)$$

wherein
E is H or $CH_3$,
G is $(CH_2)_xC(O)OSi(R)_3$ or H,
R is $CH_3$, $C_2H_5$ or $C_3H_7$,
m is an integer from 0 to 15,
x is an integer from 0 to 10, and
m+x is an integer from 1 to 15.

In accordance with a second aspect of this invention, biomedical devices, including contact lenses, are provided which are made from three-dimensional network polymerizates of (1) polysiloxanes alpha, omega terminally bonded through a divalent hydrocarbon group to an activated, unsaturated group, (2) a modulus modifier, (3) an N-alkenoyl trialkylsilyl aminate and optionally an auxiliary modifier.

The present invention provides materials which can be usefully employed for the fabrication of prostheses, such as heart valves and intraocular lenses, contact lenses or films. More particularly, the instant invention concerns hard contact lenses.

DESCRIPTION OF THE PREFERRED EMBODIMENTS

The N-alkenoyl trialkylsilyl aminates, of Formula I above, hereinafter for convenience are referred to as NATA, are a class of esterified mono- and di-carboxylic amino acids useful as a means of imparting desirable surface wetting characteristics to biomedical devices made from polysiloxane compositions. The acryloyl- and methacryloyl- mono- and dicarboxylic amino acids, hereinafter referred to as NAA, impart desirable surface wetting characteristics to the polysiloxane polymers. However, NAA quickly precipitates out of siloxane monomer mixtures before polymerization can be achieved.

It has now been found that NAA can be successfully incorporated into the polysiloxane when NAA is modified to form the trialkylsilyl esters by methods well known in the art. After the polymerization and fabrication of the biomedical device is completed, NATA is reverted to NAA by hydrolysis with or without the application of heat.

Among the amino acids found useful in this invention are monoaminomonocarboxylic acids such as glycine, alanine, 6-amino hexanoic acid and 12-aminododecanoic acid; and monoaminodicarboxylic acids, such as aspartic acid and glutamic acid. In each case, the acid contains from 1 to 15 carbon atoms exclusive of the carboxylic group(s) present. The acid is modified by the reaction of equal molar amounts of acid and methacryloyl chloride or acryloyl chloride according to processes well known in the art to obtain the desired NAA.

The desired NATA can be prepared by reacting stoichiometric amounts of NAA with the desired trialkylchlorosilane in an organic solvent at a temperature of 90°–100° C. for a period of 3 to 4 hours. The trialkylchlorosilane may have as the alkyl group methyl, ethyl, propyl or isopropyl. The organic solvent may be one such as toluene, benzene or chloroform. An organic base, such as triethyl amine is useful as an acid scavenger in the reaction. Thereafter, the product is vacuum distilled to obtain the NATA. An inhibitor such as cuprous chloride, or 2,5-diphenylbenzoquinone is added to supress polymerization during the distillation.

One or more NATA compounds are added to the siloxane/modulus modifier monomeric mixture. Depending upon the final application of the polysiloxane and the NATA employed, from 1 to 12 parts of NATA will be added to 100 parts of siloxane and modulus modifier. More preferably, the NATA will be added in an amount from about 2 to 10.5 parts while 3 to 8.2 parts of NATA are particularly useful.

The preferred siloxanes of the invention are the poly(organosiloxane)monomers disclosed in U.S. Pat. No. 4,153,641, granted May 8, 1979, and the polyparaffinsiloxane monomers disclosed in U.S. Pat. No. 4,208,506, granted June 17, 1980.

Briefly, the preferred polysiloxanes employed a poly(organosiloxanes) of the formula

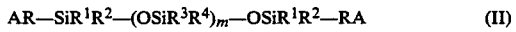

$$AR-SiR^1R^2-(OSiR^3R^4)_m-OSiR^1R^2-RA \qquad (II)$$

or polyparaffinsiloxanes of the formula

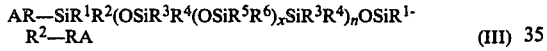

$$AR-SiR^1R^2(OSiR^3R^4(OSiR^5R^6)_xSiR^3R^4)_nOSiR^1R^2-RA \qquad (III)$$

wherein A is an activated unsaturated group; R is a divalent hydrocarbon radical having from 1 to about 22 carbon atoms $R^1$, $R^2$, $R^3$ and $R^4$ are each independently selected from the group consisting of a monovalent hydrocarbon radical having from 1 to about 12 carbon atoms and a halogen substituted monovalent hydrocarbon radical having from 1 to about 12 carbon atoms; $R^5$ and $R^6$ can be the same or different and are selected from the group consisting of hydrogen, a hydrocarbon radical containing from 1 to about 12 carbon atoms, a carboxylic acid group, a carboxylic acid ester group represented by the formula $-C(O)OR^7$ wherein $R^7$ is selected from the group consisting of a hydrocarbon group containing from 1 to about 12 carbon atoms and a carboxylic acid amide represented by the formula $-C(O)NR^8R^9$ wherein $R^8$ and $R^9$ can be the same or different and each is selected from the group consisting of hydrogen and a hydrocarbon containing from 1 to about 12 carbon atoms; x is from 2 to 25, m is an integer from 0 to 50 and n is an integer from 1 to 25. Desirably, m will be from 0 to 25 and preferably from 0 to 10. Desirably, n will be from 1 to 15 and preferably from 1 to 5. Desirably, x will be from 2 to 10 and more preferably is 2 or 3.

The term "an activated unsaturated group" refers to a group which has a substituent which functions through resonance to increase the free radical stability or activity of the double bond, thereby facilitating free radical polymerization of the monomer. These activated unsaturated groups become polymerized to form a polymer with a crosslinked three-dimensional network. Preferably the activating groups present are such that the monomers lend themselves to polymerization under mild conditions, such as ambient temperature. Preferred activating groups include: 2-cyanocryloxy, acrylonitryl, acryloaminido, acryloxy, methacryloxy, styryl and N-vinyl-2-pyrrolidinone-x-yl where x may be 3, 4 or 5.

The more preferred polysiloxane is the poly(organosiloxane) of Formula II above. In the preferred embodiment A is acryloxy or methacryloxy and more preferably methacryloxy.

R is preferably an alkylene radical. Therefore, preferably R is methylene, propylene, butylene, pentamethylene, hexamethylene, octamethylene, dodecylmethylene, hexadecylmethylene and octadecylmethylene. However, R can also be an arylene radical such as phenylene or biphenylene. More preferably R is an alkylene radical having 1, 3 or 4 carbon atoms. Most preferably R is an alkylene radical having from about 3 to 4 carbon atoms, e.g. butylene.

Preferably, $R^1$, $R^2$, $R^3$ and $R^4$ are alkyl radicals having from 1 to 12 carbon atoms, e.g. methyl, ethyl, propyl, butyl, octyl, dodecyl and the like; cycloalkyl radicals, e.g. cyclopentyl, cyclohexyl, cycloheptyl and the like; mononuclear and binuclear aryl radicals, e.g. benzyl phenylethyl, phenylpropyl, phenylbutyl and the like; alkaryl radicals, e.g. tolyl, xylyl, ethylphenyl and the like; haloaryl radicals such as chlorophenyl, tetrachlorophenyl, difluorophenyl and the like; halo substituted lower alkyl radicals having up to about four alkyl carbon atoms such as fluoromethyl and fluorpropyl. More preferably $R^1$, $R^2$, $R^3$ and $R^4$ are methyl radicals and phenyl radicals, most preferably each substituent is methyl.

Preferably $R^5$ and $R^6$ are selected from the group consisting of hydrogen, hydrocarbon containing from 1 to about 6 carbon atoms and a carboxylic acid group. More preferably $R^5$ and $R^6$ are selected from the group consisting of hydrogen and methyl.

Preferably $R^7$ is a hydrocarbon group containing from 1 to about 6 carbon atoms and most preferably is methyl.

Preferably $R^8$ and $R^9$ are each selected from the group consisting of hydrogen and hydrocarbon containing from 1 to about 4 carbon atoms. More preferably $R^8$ and $R^9$ are each selected from the group consisting of hydrogen and methyl.

The term polymerization is used to refer to the polymerization of the polysiloxanes endcapped with polymerizable activated unsaturated groups which results in a crosslinked three-dimensional polymeric network.

"A polysiloxane terminally bonded through a divalent hydrocarbon group to an activated, unsaturated group" means the described polysiloxane compound has been attached to a divalent hydrocarbon group, such as methylene or propylene, and then at the end of this group is attached an activated, unsaturated group, and this then is the most preferred siloxane monomer. Then when these monomers are polymerized (free radical polymerization) with other activated unsaturated monomers, three-dimensional polymer networks are obtained. This polymerized material is what the biomedical devices, including contact lenses, are made.

The second component of the polymer of this invention is a strength member which improves the modulus property of the polysiloxane with a minimum reduction of the oxygen permeability property. For convenience, this function is referred to as a modulus modifier. The modulus modifier is selected from the group comprising tertiary butyl styrene, a cycloalkyl modulus modifier or a polycyclic modulus modifier.

The cycloalkyl modulus modifiers are described and defined in U.S. Pat. No. 4,327,203. These modifiers are a cycloalkyl acrylate or methacrylate of the formula

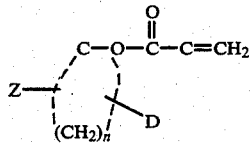

(IV)

wherein
E is either hydrogen or methyl
D is branched or normal alkyl having 3 to 6 carbon atoms, preferably 3 to 4 carbon atoms
Z is either hydrogen or methyl and
n is an integer from 3 to 8 and preferably from 4 to 6.

Illustrative of the foregoing cycloalkyl modulus modifiers are the following: Menthyl methacrylate, menthyl acrylate, tertiarybutylcyclohexyl methacrylate, isopropylcyclopentyl acrylate, tertiarypentylcycloheptyl methacrylate, tertiarybutylcyclohexyl acrylate, isohexylcyclopentyl acrylate and methylisopentyl cyclooctyl acrylate.

The polycyclic modulus modifiers are described and defined in U.S. Pat. No. 4,355,147. These modifiers are a polycyclic acrylate or methacrylate selected from the group isobornyl acrylate, isobornyl methacrylate, dicyclopentadienyl acrylate, dicyclopentadienyl methacrylate, adamantyl acrylate, adamantyl methcacrylate, isopinocamphyl acrylate and isopinocamphyl methacrylate.

The modifier is present in an amount from 90 to 10 parts by weight per 10 to 90 parts by weight of the above described polysiloxane monomers. In each event, the total parts of modifier and polysiloxane present are 100 parts. More preferably the modifier is present in the amount of 70 to 10 parts, more preferably yet the modifier is 45 to 15 parts.

The relative hardness (or softness) of the contact lenses, i.e. polymer of this invention can be varied by the amount of modulus modifier employed. Further small changes in the relative hardness can be obtained by decreasing or increasing the molecular weight of the monomeric polysiloxane endcapped with the activated, unsaturated groups. As the ratio of siloxane units to endcap units increases, the softness of the material increases. Conversely, as this ratio decreases, the rigidity and hardness of the material increases.

The above polymer system contains from zero to 20 parts by weight, based on weight of polysiloxane and modulus modifier, of an auxiliary modifier. These auxiliary modifiers are reactive with the three components of this invention. Minor but often desirable changes of physical properties, e.g. tear strength and tensile strength, are obtained by the use of auxiliary modifiers.

Useful auxiliary modifiers include, but are not limited to, tertiary-butyl acrylate, polyethylene glycol acrylate, hydroxyethyl methacrylate, polyethylene glycol diacrylate, polyethylene glycol methacrylate, polyethylene glycol dimethacrylate, divinyl benzene, neopentylglycol diacrylate, ethylene glycol dimethacrylate, ethylene glycol diacrylate, neopentylglycol dimethacrylate, polyvinyl alkyl benzenes, especially divinyl alkyl benzenes, e.g. divinyl toluene, 1,4-butane diglycol dimethacrylate and mixtures thereof. The foregoing polyethylene glycols will contain from 2 to 9 repeating ethylene glycol units.

The polysiloxanes alpha, omega terminally bonded through a divalent hydrocarbon group to an activated unsaturated group, i.e. the monomers herein, are generally clear, colorless liquids, whose viscosity depends on the value of m or n. These monomers can be readily cured to cast shapes by conventional methods, such as free radical initiators. Illustrative of free radical initiators which can be employed are bis(isopropyl)peroxydicarbonate, azo-bisisobutyronitrile, acetyl peroxide, lauroyl peroxide, decanoyl peroxide, benzoyl peroxide, benzoin methyl ether, diethoxyacetophenone, tertiary butyl peroxypivalate and the like. The monomers are cured through the well known methods of heat and/or actinic light, depending on the nature of the catalyst.

The advantages of using the contact lenses, i.e. polymers of the instant invention which are made from the monomers disclosed herein are numerous. For example, (1) the advantages of using activated vinyl terminal groups to cure the siloxane material are (a) the high reactivity systems permit rapid cure at or near room temperature if suitable initiators are used, (b) no fillers are needed to get useful physical strength as is common with most silicone resins in contact lenses. This is desirable since the use of fillers requires that other possibly undesirable materials be added to the composition in order to match the refractive index of the polymer to the filler.

Secondly, the contact lenses made from the polymer of the instant invention are oxygen permeable. A critical oxygen tension and flux under a lens should be about 10 mm Hg and 2 ml/(cm$^2$hr.) respectively below which corneal swelling occurs. Polse and Decker, Investigative Ophthalmology and Visual Science, vol. 18, p 188, 1979. In order to meet these requirements, the lens material must have adequate oxygen permeability. When m in formula II and n in III above are at least about 2, the chain of siloxane is long enough in the instant composition to exceed the oxygen requirements of the cornea. However, in specific situations m and n may be as low as 0.

Additionally, these lenses are hydrolytically stable meaning that when the contact lenses are placed into an aqueous solution, e.g. on the eye, or during the disinfecting step, i.e. water plus heat, the lenses will not change in chemical composition, i.e. hydrolyze.

The most preferred contact lens of the instant invention is a fillerless, oxygen permeable, hydrolytically stable, wettable, biologically inert, transparent, hard, polymeric contact lens comprising a poly(organosiloxane) terminally bonded through a divalent hydrocarbon group to a polymerized activated, unsaturated group. These most preferred contact lenses have an oxygen permeability of at least $10 \times 10^{-11}$ cm$^3$cm/(sec.cm$^2$ mmHg), are hydrolytically stable, biologically inert and transparent.

The polymers of this invention can be formed into contact lenses by the spincasting process as disclosed in U.S. Pat. Nos. 3,408,429 and 3,496,254 and other conventional methods such as compression molding as disclosed in U.S. Pat. Nos. 4,085,459 and 4,197,266.

When the term "shaped article for use in biomedical applications" or "biomedical device" are used herein, it is meant that the materials disclosed herein above have physiochemical properties rendering them suitable for prolonged contact with living tissue, blood and the mucous membrane. These properties are required for biomedical shaped articles, such as surgical implants, blood dialysis devices and membranes intended to come in contact with body fluid outside of the body, e.g. membranes for kidney dialysis and heart/lung machines and the like. It is known that blood, for example, is rapidly damaged in contact with artificial surfaces. The design of a synthetic surface which is antithrombogenic and nonhemolytic to blood is necessary for prostheses and devices used with blood. The instant polymers are compatible with living tissue.

The polymers disclosed herein can be boiled and/or autoclaved in water without being damaged whereby sterilization may be achieved. Thus, an article formed from the disclosed polymers may be used in surgery where an article compatible with living tissue or with the mucous membrane may be used.

The following examples are illustrative only and should not be construed as limiting the invention. All parts and percents referred to herein are on a weight basis, all viscosities measured at 25° C. unless otherwise specified and all temperatures are degrees Celsius.

EXAMPLE I

Step A

Synthesis of N-Methacryloylglutamic Acid

Sodium hydroxide, 120 grams (3.0 mole), is added to 2,000 ml of water in a 5,000 ml four neck round bottom flask equipped with a mechanical overhead stirrer and thermometer. The solution is cooled to $\leq 5°$ C. using an ice-methanol bath. To this is added 500 g (3.0 mole) of L-glutamic acid monosodium salt and 0.6 gram of methoxyhydroquinone. Then 347 g of methacryloyl chloride (324 ml, 3.3 mole) are slowly added to the above reaction until a pH of 10 is reached. At this point, a solution of 160 grams of sodium hydroxide in 350 ml of water is added simultaneously with the remaining chloride to maintain a pH between 8 and 10. Temperature throughout the addition (2 hours) should be maintained at $\leq 5°$ C. The exotherm is controlled by adjusting the rate of addition of the two reactants.

After all the methacryloyl chloride has been added, the sodium hydroxide addition continues until a stable 9–10 pH is achieved. At this point, the reaction solution is allowed to obtain room temperature for an additional hour and then slowly acidified to pH of 2–3 using concentrated (12N) HCL. The acidified solution is saturated with sodium chloride (approx. 350 g) and divided in half. Each half is extracted three times using 700 ml of ethyl acetate. This step should be carried out expediently to minimize hydrolysis.

The combined organic layer is washed once with 100 ml of a saturated sodium chloride solution and dried over anhydrous magnesium sulfate for thirty minutes with stirring. The dried solution is filtered through a sintered glass filter (350 ml—coarse) and evaporated in vacuo (Rotovapor) to 500 ml volume to produce white crystals. It becomes necessary during the devolatilization to periodically filter out formed crystals to avoid bumping. The combined crystals are added to a 500 ml round bottom flask with adaptor and connected to high vacuum for three hours. This is the first crop of crystals. The melting range should be 128°–130° C. NMR analysis is also done. The filterate is stored in the refrigerator overnight to produce a second crop of crystals. These are treated in the same way as the first crop.

Step B

Synthesis of Trimethylsilyl N-Methacryloylglutamate

N-Methacryloyl-L-glutamic acid (30 g, 0.24 mol.) and an excess amount of hexamethyldisilazane (60 ml) are placed in a 250 ml round bottom flask equipped with a condenser, drying tube (Drierite), and magnetic stirrer. Cuprous chloride (500 ppm) is added as an inhibitor. The above suspended reaction mixture is heated to 80° C. for two hours, cooled to 40° C. and on Rotovapor attached to house vacuum line (cold trap) with a dry nitrogen bleed.

The remaining viscous material is transferred under dry nitrogen subjected to a high vacuum distillation. The distillation temperature is 130°–135° C./0.05 mmHg (oil bath) 150°–160° C. NMR and infrared spectra confirm the product is bis-trimethylsilyl N-methacryloylglutamate.

EXAMPLE II

To a reaction vessel containing chloroform is charged 5 g (0.035 moles) of N-methacryloylglycine, 7 ml (0.042 moles) triethylchlorosilane and 5.8 ml (0.42 moles) triethyl amine. The reaction is continued for five hours at 100° C. The inhibitor 2,5-diphenylbenzoquinone is added to supress polymerization. The reaction mixture is cooled down with an ice bath and washed with ice cold water. The organic layer is separated and then dried over magnesium sulfate and evaporated to dryness. High vacuum distillation is then applied. The triethylsilyl ester of N-methacryloylglycine, boiling point 107° C./0.05 mmHg, is obtained. NMR and infrared spectra confirm the structure.

EXAMPLE III

To a reaction vessel is charged 15 g of N-methacryloyl-6-aminohexanoate and 50 g hexamethyldisilazane. The mixture is heated at 90° C. for one hour while stirring and the volatile materials are removed in vacuo. The residue is distilled under high vacuum to yield trimethylsilyl N-methacryloyl-6-aminohexanoate having a boiling point of 118° C./0.05 mmHg. NMR and infrared spectra confirm the structure.

EXAMPLE IV

Following the procedure of Example III, trimethylsilyl-N-methacryloyl-12-aminododecanoate is prepared from N-methacryloyl-12-aminododecanoic and hexamethyldisilazane. The NMR spectrum is consistent with the prepared compound.

EXAMPLE V

Following the procedure of Example I, bis-trimethylsilyl N-methacryloyl aspartate is prepared from N-methacryloyl aspartanoic acid and hexamethyldisilazane. Boiling point is 110°–114° C./.025 mmHg. NMR spectra confirmed the structure of the above compound.

PREPARATION OF POLY(ORGANOSILOXANE)MONOMERS

Preparation of various poly(organosiloxane)monomers within the scope of Formula II above are shown in Examples VI through VIII below. These monomers are used in preparing the polysiloxane compositions of the invention.

EXAMPLE VI

A di(organosiloxane)monomer within the scope of Formula II above, wherein $R^1$ and $R^2$ are methyl, R is butyl and A is methacryloxy, is prepared by charging 557 g of 1,3-bis(4-hydroxybutyl)tetramethyl disiloxane, 634 g of dry pyridine and 2 liters of hexane to a 5 liter reaction flask equipped with a mechanical stirrer and drying tube. The mixture is chilled to 0° C. and then 836 g of methacryloyl chloride is added dropwise. The mixture is agitated continuously overnight. The reaction solution is extracted consecutively with 10% water solutions of HCl and $NH_3$ in order to remove excess reagents and pyridine hydrochloride. The resulting solution of the product in hexane is dried with anhydrous $MgSO_4$, filtered, and solvent removed at reduced pressure. About 459 g (55% yield) of 1,3-bis(4-methacryloxy butyl)tetramethyl disiloxane is collected. The structure is confirmed by infrared spectra, proton magnetic resonance spectra and elemental analysis. IR spectra shows no intense hydroxyl band between 3100 and 3600 $cm^{-1}$ but does show strong methacrylate absorptions at 1640 and 1720 $cm^{-1}$. NMR spectra agrees with the structure.

EXAMPLE VII

To a three-neck vessel equipped with a mechanical stirrer and calcium sulfate drying tube is charged 810.1 parts of octamethylcyclotetrasiloxane, 182.8 parts of 1,3-bis(4-methacryloxybutyl)tetramethyl disiloxane and 2.5 parts of trifluoromethane sulfonic acid. The reaction proceeds at room temperature. After a reaction time of three hours, the catalyst is neutralized with a 10 fold excess (13.9 parts) of sodium bicarbonate. Stirring is continued for about three hours to insure complete neutralization. The crude reaction product is filtered through a column packed with Celite ® brand diatomaceous earth and activated alumina (Alcoa F20 grade). The resulting filtrate is freed of volatiles by passing it over a thin film evaporator operating at 110° C. temperature and 0.25 torr pressure. The product has a viscosity of 0.28±0.05 stokes and approximately 25 dimethylsiloxy repeating units.

EXAMPLE VIII

Example VII is repeated except that 890.4 parts of octamethylcyclotetrasiloxane and 100.6 parts of 1,3-bis(4-methacryloxybutyl)tetramethyl disiloxane are used. The resulting product has approximately 50 dimethylsiloxy repeating units.

POLYMERIC COMPOSITIONS OF THIS INVENTION

EXAMPLE IX

A solution containing 60 parts of isobornyl methacrylate (hereinafter referred to as IBOMA), 30 parts of the di(organo-siloxane)monomer of Example VII, 10 parts of ethylene glycol-dimethacrylate (hereinafter referred to as EGDMA and 5 parts of trimethylsilyl N-methacryloyl glutamate (hereinafter referred to as TMSMG), 0.5 parts of benzoin methyl ether (hereinafter referred to as BME) and 0.5 parts of di(sec-butyl)peroxy-dicarbonate (hereinafter referred to as BPC) is mixed together, degassed and cast into a film between glass plates. The casting is maintained at ambient temperature under ultraviolet light for half an hour and then post cured at 140° C. for one hour before removing from the mold. Physical test values obtained on the film are as follows:

Tensile Strength, Ultimate: 2,500 $g/mm^2$
Modulus: 130,000 $g/mm^2$
Elongation, Ultimate: 2.6%
Oxygen Permeability: 3.0×PHEMA
Oleic Acid Uptake: 2.9%

A typical oxygen permeability value for PHEMA (polyhydroxyethyl methacrylate) hydrogel is $8.0 \times 10^{-11}$ $cm^3$ cm/(sec. $cm^2$ mmHg). The oxygen permeability measurements were made using a flat polarographic sensor. The method used was basically that described by Refojo et al (Refojo, M. Holly, F., and Leong, F-L., Contact and Intraocular Lens Medical Journal, Vol. 3, issue 4, p 27 (1977). The values have been corrected to sample thickness.

Oleic acid uptake, weight percent, is also a measure of the suitability of the polymers of this invention for use as a contact lens, since the fluids around the eye contain varying amounts of oleic acid. This test is carried out by immersing a weighed sample in oleic acid for 18 hours, maintained at 35° C. The sample's surface is cleaned of oleic acid and weighed again. The lower the oleic acid uptake value, the greater the dimensional stability of a contact lens made from the polymer will be.

The polymer of this example is suitable for use as a hard, gas permeable contact lens.

EXAMPLE X

Following the procedure of Example IX, additional polymeric compositions are prepared using 70 parts of di(organosiloxane)monomer of Example VII, 15 parts IBOMA, 15 parts of EGDMA, 0.5 parts of BME and the N-alkenoyl trialkylsilyl aminate (hereinafter ATSA) as indicated below:

| ATSA | | Modulus, | Contact[1] |
|---|---|---|---|
| Parts | Of Example | $g/mm^2$ | Wetting Angle |
| 2.7 | II | 92,850 | 51° |
| 5.4 | II | 94,000 | 56° |
| 10.8 | II | 98,680 | 47° |
| 5.0 | I | 91,000 | 53° |

[1] Hydrolyzed at 50° C. overnight in distilled water prior to measuring contact wetting angle. Air bubble in saline water method.

The polymers of this example are suitable for use as a contact lens.

EXAMPLE XI

Using the method of Example IX, a polymeric composition of 70 parts of the di(organosiloxane)monomer of Example VI, 15 parts IBOMA, 15 parts EGDMA and 5 parts of TMSMG is prepared. The catalyst is BME. The film is cured two hours at ambient temperature with ultraviolet light, followed by one hour at 80° C. with ultraviolet light. Physical test values obtained on the film are as follows:

Modulus: 85,400 $g/mm^2$
Elongation, Ultimate: 0.6%
Oxygen Permeability: 1.6×PHEMA
Oleic Acid Uptake: 0.81%

Another portion of the monomer mixture is injected into a contact lens mold mounted on a spinner. The composition is spun cured with the ultraviolet light for 10 minutes to obtain contact lenses. The lenses are then immersed in hot water (about 50° C.) for an hour to extract any residual monomers and deblock or convert the TMSMG by removal of the trimethylsilyl groups to reform the free acid groups, i.e. N-methacryloylglutamic acid. The resulting hard, gas permeable lens is suitable for use.

EXAMPLE XII

A monomer solution similar to that of Example IX is cast as a rod by filling a vial 2 cm in diameter and 5 cm in height and curing in a water bath at 32° for 3 days and at 45° for 2 days followed by post-curing in an air oven at 60° C. for one hour. During the next hour, the temperature is raised gradually to 100° C. followed by one hour at 110° C. The resultant optically clear rod is lathe cut into buttons from which suitable hard contact lenses are fabricated.

EXAMPLE XIII

A monomeric solution is prepared by mixing together 41.7 parts of a poly(organosiloxane)monomer similar to that of Example VII except that the number of dimethylsiloxy repeating units is 10, 45.8 parts of IBOMA, 12.5 parts of EGDMA, 5 parts of TMSMG and 0.5 parts BPC. The solution is degassed and cast into a film between glass plates. The casting is heat cured for two hours with a temperature rise from 60° C. to 120° C. The polymer is clear and suitable for contact lenses. Physical test values obtained on the film are as follows:
 Modulus: 105,000 g/mm$^2$
 Elongation, Ultimate: 1.2%
 Oxygen Permeability: 3.5×PHEMA
 Oleic Acid Uptake: 2.4%

EXAMPLE XIV

A composition similar to Example XIII is prepared except that the ATSA is that of Example III. The resulting polymer is suitable for contact lenses and other biomedical devices.

EXAMPLE XV

A monomeric solution is prepared by mixing together 52 parts of a poly(organosiloxane)monomer similar to that of Example VII except that the number of dimethylsiloxy repeating units is 4, 38 parts of IBOMA, 10 parts of EGDMA, 5 parts of TMSMG and 0.5 parts BME. The solution is degassed and cast into a film between glass plates. The casting is cured for two hours at ambient temperatures with ultraviolet light. The polymer is clear and suitable for contact lenses. Physical test values obtained on the film are as follows:
 Modulus: 104,000 g/mm$^2$
 Elongation, Ultimate: 2.5%
 Oxygen Permeability: 1.7×PHEMA
 Oleic Acid Uptake: 4.0%

EXAMPLE XVI

A composition similar to Example XIII is prepared except that the ATSA is that of Example IV. The reslting polymer is suitable for contact lenses and other biomedical devices.

EXAMPLE XVII

A monomeric solution is prepared by mixing together 80 parts of the poly(organosiloxane) of Example VI, 20 parts of teritary butyl cyclohexyl methacrylate, 5 parts of TMSMG and 0.5 parts BPC. The solution is degassed and cast into a film between glass plates. The casting is heat cured for two hours with a temperature rise from 60° C. to 120° C. The polymer is clear and suitable for contact lenses. Physical test values obtained on the film are as follows:
 Modulus: 76,700 g/mm$^2$
 Elongation, Ultimate: 3.3%
 Oxygen Permeability: 2.0×PHEMA
 Oleic Acid Uptake: 4.7%

EXAMPLE XVIII

A monomeric solution is prepared by mixing together 60 parts of the poly(organosiloxane) of Example VI, 40 parts of tertiary butyl cyclohexyl methacrylate, 5 parts of TMSMG and 0.5 parts BPC. The solution is degassed and cast into a film between glass plates. The casting is heat cured for two hours with a temperature rise from 60° C. to 120° C. The polymer is clear and suitable for contact lenses. Physical test values on the film are as follows:
 Modulus: 97,700 g/mm$^2$
 Elongation, Ultimate: 3.4%
 Oxygen Permeability: 1.4×PHEMA
 Oleic Acid Uptake: 5.4%

EXAMPLE XIX

A composition similar to Example XIII is prepared except that the ATSA is that of Example V. The resulting polymer is suitable for contact lenses and other biomedical devices.

EXAMPLE XX

A composition similar to Example XIII is prepared except that the siloxane is a polyparaffinsiloxane of Formula III and prepared according to Example II of U.S. Patent No. 4,208,506 and the number of paraffinsiloxane repeating groups is 10. The resulting polymer is suitable for contact lenses.

EXAMPLE XXI

A composition similar to Example XX is prepared except that the ATSA is that of Example V. The resulting polymer is suitable for contact lenses.

The preceding Examples and methods have been described in the foregoing specification for the purpose of illustration and not limitation. Other modifications and ramifications will naturally suggest themselves to those skilled in the art based on the disclosure. These are intended to be comprehended within the scope of this invention.

The embodiments of the invention in which an exclusive property or privilege is claimed or defined as follows:

1. In a shaped article for use in biomedical applications being a polymer formed by polymerizing (a) one or more polysiloxane monomers alpha, omega terminally bonded through divalent hydrocarbon groups to an activated unsaturated group with (b) a modulus modifier to form a crosslinked three-dimensional polymeric network, said modulus modifier being present in an amount from 90 to 10 parts per 10 to 90 parts of polysiloxane monomers and the sum of parts equals 100, and (c) from zero to 20 parts per 100 parts of modulus modifier and polysiloxane monomers of an auxiliary modifier, the improvement which comprises incorporating from 1 to 12 parts per 100 parts of modulus modifier and polysiloxane monomers in the monomer mixture to be polymerized of one or more N-alkenoyl trialkylsilyl aminates of the formula

wherein
E is H or CH$_3$,
G is (CH$_2$)$_x$C(O)OSi(R)$_3$ or H,
R is CH$_3$, C$_2$H$_5$ or C$_3$H$_7$,
m is an integer from 0 to 15,
x is an integer from 0 to 10, and
m+x is an integer from 1 to 15.

2. The article of claim 1 wherein E of the aminate is CH$_3$.

3. The article of claim 2 wherein G of the aminate is (CH$_2$)$_x$C(O)OSi(R)$_3$.

4. The article of claim 3 wherein the aminate is of the formula $$CH_2=C(CH_3)C(O)N(H)CH[C(O)OSi(C_2H_5)_3]CH_2\text{-}C(O)OSi(C_2H_5)_3.$$

5. The article of claim 3 wherein the aminate is of the formula $$CH_2=C(CH_3)C(O)N(H)CH[\text{-}C(O)OSi(CH_3)_3](CH_2)_2C(O)OSi(CH_3)_3.$$

6. The article of claim 2 wherein G of the aminate is H.

7. The article of claim 6 wherein the aminate is of the formula $$CH_2=C(CH_3)C(O)N(H)CH_2C(O)OSi(C_2H_5)_3.$$

8. The article of claim 6 wherein the aminate is of the formula
$$CH_2=C(CH_3)C(O)N(H)CH_2(CH_2)_6\text{-}C(O)OSi(CH_3)_3.$$

9. The article of claim 6 wherein the aminate is of the formula $$CH_2=C(CH_3)C(O)N(H)(CH_2)_{11}C(O)OSi(CH_3)_3.$$

10. The article of claim 1 wherein E of the aminate is H.

11. The article according to claim 1 wherein the polysiloxane is a poly(organosiloxane) of the formula $$AR\text{—}SiR^1R^2\text{—}(OSiR^3R^4)_m\text{—}OSiR^1R^2\text{—}RA$$

wherein A is an activated unsaturated group, R is a divalent hydrocarbon radical having from 1 to about 22 carbon atoms, R$^1$, R$^2$, R$^3$ and R$^4$ can be the same or different and each is a monovalent hydrocarbon radical or a halogen substituted monovalent hydrocarbon radical each having from 1 to about 12 carbon atoms and m is an integer from 0 to 50.

12. The article according to claim 1 wherein the polysiloxane is a polyparaffinsiloxane of the formula $$AR\text{—}SiR^1R^2(OSiR^3R^4(OSiR^5R^6)_xSiR^3R^4)_nOSiR^1R^2\text{—}RA$$

wherein A is an activated unsaturated group; R is a divalent hydrocarbon radical having from 1 to about 22 carbon atoms; R$^1$, R$^2$, R$^3$ and R$^4$ are each independently selected from the group consisting of a monovalent hydrocarbon radical having from 1 to about 12 carbon atoms and a halogen substituted monovalent hydrocarbon radical having from 1 to about 12 carbon atoms; R$^5$ and R$^6$ can be the same or different and are selected from the group consisting of hydrogen, a hydrocarbon radical containing from 1 to about 12 carbon atoms, a carboxylic acid group, carboxylic acid ester group represented by the formula —C(O)OR$^7$ wherein R$^7$ is selected from the group consisting of a hydrocarbon group containing from 1 to about 12 carbon atoms and a carboxylic acid amide represented by the formula —C(O)NR$^8$R$^9$ wherein R$^8$ and R$^9$ can be the same or different and each is selected from the group consisting of hydrogen and a hydrocarbon group containing from 1 to about 12 carbon atoms; x is 2 or greater and n is an integer of 1 to about 25.

13. Wherein the article according to claim 1 is a gas permeable hard contact lens.

14. The article according to claim 1 wherein the auxiliary modifier is ethylene glycol dimethacrylate.

15. In a shaped article for use in biomedical applications being a polymer formed by polymerizing (a) one or more polysiloxane monomers alpha, omega terminally bonded through divalent hydrocarbon groups to an activated unsaturated group with (b) a modulus modifier to form a crosslinked three-dimensional polymeric network, said modulus modifier being present in an amount from 90 to 10 parts per 10 to 90 parts of polysiloxane monomers and the sum of parts equals 100, and (c) from zero to 20 parts per 100 parts of modulus modifier and polysiloxane monomers of an auxiliary modifier, the improvement which comprises having incorporated therein from 1 to 12 parts per 100 parts of modulus modifier and polysiloxane monomers in the polymerized monomer mixture one or more N-alkenoyl aminoic acids or the salts thereof, of the formula $$CH_2=C(E)C(O)N(H)CH(G)(CH_2)_mC(O)OH$$

wherein
E is H or CH$_3$,
G is (CH$_2$)$_x$C(O)OH, or H,
m is an integer from 0 to 15,
x is an integer from 0 to 10, and
m+x is an integer from 1 to 15.

16. Wherein the article according to claim 15 is a gas permeable hard contact lens.

17. The contact lens of claim 16 wherein the auxiliary modifier is ethylene glycol dimethacrylate.

18. Wherein the contact lens of claim 17 contains the N-alkenoyl aminoic acid of the formula $$CH_2=C(CH_3)C(O)N(H)CH[C(O)OH](CH_2)_2\text{-}C(O)OH.$$

* * * * *